(12) United States Patent
De Domenico (10) Patent No.: US 8,702,599 B2
(45) Date of Patent: Apr. 22, 2014

(54) LARYNGOSCOPE, COMPRISING A SET OF MAGNETIC ELEMENTS

(76) Inventor: Andrea De Domenico, Rome (IT)

( * ) Notice: Subject to any disclaimer, the term of this patent is extended or adjusted under 35 U.S.C. 154(b) by 289 days.

(21) Appl. No.: 13/143,894

(22) PCT Filed: Apr. 15, 2009

(86) PCT No.: PCT/IT2009/000163
§ 371 (c)(1),
(2), (4) Date: Sep. 21, 2011

(87) PCT Pub. No.: WO2010/079521
PCT Pub. Date: Jul. 15, 2010

(65) Prior Publication Data
US 2012/0022332 A1    Jan. 26, 2012

(30) Foreign Application Priority Data
Jan. 12, 2009  (IT) .............................. RM2009A0010

(51) Int. Cl.
*A61B 1/267* (2006.01)
(52) U.S. Cl.
USPC .......................................................... 600/194
(58) Field of Classification Search
USPC .......................... 128/200.26, 207.14–207.17; 600/185–200, 424
See application file for complete search history.

(56) References Cited

U.S. PATENT DOCUMENTS

| 3,674,014 A | | 7/1972 | Tillander | |
|---|---|---|---|---|
| 4,063,561 A | * | 12/1977 | McKenna | 128/207.15 |
| 4,244,362 A | * | 1/1981 | Anderson | 128/200.26 |
| 5,257,636 A | * | 11/1993 | White | 128/897 |
| 6,173,199 B1 | * | 1/2001 | Gabriel | 600/424 |
| 6,715,491 B2 | * | 4/2004 | Cooper et al. | 128/207.14 |
| 2003/0154985 A1 | * | 8/2003 | Cooper et al. | 128/207.14 |

FOREIGN PATENT DOCUMENTS

| EP | 1433413 A2 | 6/2004 |
|---|---|---|
| GB | 2105994 A | 4/1983 |
| WO | 2007146469 A1 | 12/2007 |

OTHER PUBLICATIONS

Search Report; Application No. ITRM20090010.
International Preliminary Report; Application No. PCT/IT2009/000163.

* cited by examiner

*Primary Examiner* — Christopher Beccia
(74) *Attorney, Agent, or Firm* — Waters & Associates, PLC (57) ABSTRACT

An improved laryngoscope that is useful in endotracheal intubation. The laryngoscope includes an inner magnetic element that is situated at an end of the laryngoscope's blade and an outer magnetic element that is positioned on a patient's throat in such a manner that the interaction between the inner and outer elements attracts the end of the blade toward the patient's epiglottic vallecula when the blade is moved into the patient's throat. The blade also includes a magnetic bed located along its longitudinal axis. The magnetic bed is designed to interact with a metallic spiral tube and, by means of this interaction, guide the tube properly in the patient's inner air tract. The blade also includes at least three coplanar elements that able to rotate relative to each other. The adjustment of these elements increases the blade's usefulness for moving the patient's tissues and opening a passage to the patient's trachea.

9 Claims, 6 Drawing Sheets

LARYNGOSCOPE, COMPRISING A SET OF MAGNETIC ELEMENTS

CROSS-REFERENCE TO RELATED APPLICATIONS

This application is the U.S. National Phase under 35. U.S.C. §371 of International Application PTC/IT2009/000163, filed Apr. 15, 2009, which claims priority to Italian Patent Application RM2009A000010, filed Jan. 12, 2009. The International Application was published under PCT Article 21(2) in English.

TECHNICAL FIELD

The present invention concerns a medical device that is particularly suitable for endotracheal intubation of a patient. More in particular, it concerns an improved laryngoscope that comprises a magnetic element, placed at its own extremity, and that interacts with an outer magnetic element, so that the position of the entire instrument is properly guided inside the mouth and the upper air tract of a patient.

The same device comprises a set of additional magnetic elements, placed along the so called blade, that are particularly suitable to address, according to a proper direction, the insertion of an endotracheal tube. The same blade is characterized by an articulated structure, in respect of one or more pivots, so that it is possible to adjust the geometrical shape of the instrument, with reference to some specific anatomical conformations of some patients, or specific situations that result as operatively difficult.

BACKGROUND ART

As known, the laryngoscope is an instrument used in particular by a physician in order to visualize the glottis (that is usually impossible to see) and the vocal cords. It basically comprises two parts: the handle, where a set of batteries are installed inside; and the blade, that is the part inserted inside the mouth of a patient, and that further includes a small light bulb being able to enlight the inner part of the larynx. The laryngoscope is an essential instrument for endotracheal intubation of a patient, and that means everytime it is required a direct connection of the air tracts with instruments able to support the ventilation. In order to obtain this result, normally a flexible tube is inserted, the so called endotracheal tube, that is gradually pushed inside the air tracts, beyond the epiglottis and the vocal cords, until it reaches the first tract of trachea with an extremity, while the other extremity is kept outside of the patient, in order to connect, i.e., a machine able to support ventilation.

In this procedure it is very important that said inner extremity reaches the proper position, and that is not sent by mistake to the esophagus, causing consequent huge problems to the patient. Further, intubation is a very critical procedure, because important anatomical parts are touched, like i.e. the vocal cords, that absolutely should not be hurt by passage of the above instruments. Furthermore, usually this procedure must be done as fast as possible, in order to guarantee a proper ventilation of the patient.

Another important point is that glottic and paraglottic structures are not easy to be visualized, sometimes a physician should follow the procedure without a complete view of these structures, i.e. because of the specific anatomy of some patients, or because of specific situations, like i.e. seriously injured people, where the head and cervical part of vertebral column are required to be blocked, in such a way that specific actions of physicians (like i.e. extension of the atlanto-occipital joint while bending forward the lower tract of the cervical column) are difficult, these actions are usually done in order to have a more effective laryngoscopy, using a laryngoscope, before to place an endotracheal tube. Furthermore, the above situations can occur simultaneously, or one can be more relevant than others, up to extreme situations, like i.e. in a emergency where a physician cannot visualize any glottic structures, and it is necessary to operate almost in a blindness situation, placing the laryngoscope and the endotracheal tube trusting more in personal experience and ability, than in a direct view of such structures.

Again, considering a possibility, absolutely not remote in a seriously injured patient, of a huge bleeding in the upper air tracts or immediately adjacent structures, where a hematic diffusion occurs in glottic and paraglottic parts, then the situation of a low or null view of these anatomical structures brings to a condition of relative useless for advanced and modern technologies like i.e. that based on optical devices (fiberscopes and video-laryngoscopes). At this point, the physician has the only choice, before to start techniques of tracheostomy in a emergency, of going for an attempt of blind intubation, using one of the well known techniques for these situations (fast track, track light, both laryngoscope and tube-stylet devices).

Actually, one of the best known intubation techniques is based on the so called stylet, which is a rigid metallic wire, fixed inside an endotracheal tube. This endotracheal tube, with the above said stylet fixed inside, can be properly shaped by a physician, and then inserted, with the visual help of a laryngoscope, inside the mouth of a patient, pushing the extremity towards the trachea. This procedure could require a certain number of different attempts by medical staff, and each time the proper position of the endotracheal tube should be verified, eventually extracting and inserting it again and again, until the profile is compatible with the air tracts of the patient.

Naturally, each of the above attempts increases the possibility of hurting some important tissues, like i.e. the vocal cords, and it makes the intubation procedure very hard and difficult for medical staff. This procedure requires at least the simultaneous action of two doctors, where the first applies the laryngoscope, in order to see and follow the best direction for the endotracheal tube, while the second is responsible for removing the stylet at the end of operations.

Thus, both the multiple attempts and the need for two doctors, that should coordinate their respective actions, increase the final execution time for this procedure, and increase the consequent possibility of direct or indirect complications for the same patient.

In the prior art, the problem of finding a new method, or medical device, suitable to improve the actual endotracheal intubation of a patient, is particularly known and important. Some solutions have been proposed in order to obtain an indirect guide, based on outer magnets, and giving the possibility of installing an endotracheal tube in the proper place. For example, U.S. Pat. No. 4,063,561 describes an outer magnet, able to interact with the lower extremity of an endotracheal tube, during the process of patient intubation. This magnet is especially useful in order to avoid a wrong direction towards the esophagus. In U.S. Pat. No. 4,244,362 a similar solution is described, where a stylet is inserted inside an endotracheal tube, that is placed along the air tracts of a patient. At the extremity of the same stylet it is placed an inner magnetic element, so that it can interact with an outer magnetic element. This stylet presents a profile able to shape an endotracheal tube, in order to provide a proper intubation of the same patient.

U.S. Pat. No. 4,244,362 describes a system useful to define the proper direction of an endotracheal tube during the operations of patient intubation. It comprises a flexible stylet with a first magnet, placed at its own extremity, and an outer structure, similar to a collar, with a second magnet placed close to the crico-thyroid membrane. The alignment of magnets guides the stylet towards the best direction, and permits to insert the endotracheal tube in the proper position.

Again, in order to improve the actual procedures of patient intubation, some other solutions are known where the laryngoscopes have a specific variable blade's profile, that is particularly useful to move inner tissues of the patient. In example, the so called McCoy laryngoscope has an original mechanism, as described in U.S. Pat. No. 4,573,451, where the remote extremity of the blade can be rotated up, using a specific lever placed behind the handle.

All these known solutions have a certain number of drawbacks, in example:
- the inner magnetic element is placed on a specific element, that is a stylet, and it must be removed in order to leave the endotracheal tube alone; this step where the stylet is removed and then inserted again, increases the execution time of the complete procedure, and increases the risk of hurting inner tissues of the patient;
- the outer magnetic element is placed close to the crico-thyroid membrane, that is a good point to indicate the final position of an endotracheal tube, but it does not give any advantage to physicians, with reference to the problem of reaching the same point, through tissues that can obstruct the air tracts of the patient;
- the use of a certain number of instruments, that are a laryngoscope, an endotracheal tube, a stylet and an outer magnet, requires the coordination of at least two doctors, with consequent difficulty for the operations of intubation;
- the outer magnetic element represents a reference point for positioning the tube towards the trachea, but it does not avoid the problem of reaching that point, that requires a certain number of attempts, where the endotracheal tube, with the stylet inside, is removed and inserted again and again, until the profile is perfect in respect of the air tracts of the patient.

All these drawbacks are critical for the ideal characteristics of an endotracheal intubation procedure, that should be fast, precise and effective, without damage or side effects for the patient.

DISCLOSURE OF INVENTION

Therefore, the main objective of the present invention is to overcome all the above described drawbacks, proposing an improved laryngoscope, suitable for an endotracheal intubation of a patient, where the position of the blade's extremity is guided by an outer magnetic element, towards the so called epiglottic vallecula.

Another objective of invention is that, once placed, the same device can be used to move the patient's anatomical tissues that are close to the epiglottic vallecula, pulling the epiglottis down, and opening consequently a passage to trachea of the same patient. This procedure can give a better view of larynx and other inner anatomical parts of the patient.

Another objective is that the same laryngoscope can guarantee a directional guide, all during the time of insertion of the same endotracheal tube inside the patient's mouth and air tracts.

Another further objective is that the use of laryngoscope results to be particularly fast, precise and comfortable, and allows an intubation procedure that is executed by a unique physician.

Therefore, it is specific subject of the present invention an improved laryngoscope, especially suitable to be used in a procedure of endotracheal intubation of a patient, comprising:
- a handle, where a set of batteries are installed inside; and a blade, jointed to said handle with a "L" shape, including a small light bulb having its terminals that are electrically connected to respective poles of said set of batteries; said blade being pushed inside the patient's mouth, and said light bulb being able to enlight the inner parts of the same patient;

wherein:
- said blade comprises an inner magnetic element that is situated distally at its own extremity, and being able to interact with an outer magnetic element that has an opposite pole, and that is placed at the outer front part of the same patient, touching his throat, immediately under the hyoid bone and oriented in direction of the thyrohyoid membrane, so that said extremity of blade is subject to an attractive force, created by interaction of said inner and outer magnetic elements, and it is consequently placed close to the anatomical part of the patient so called epiglottic vallecula.

Further, according to the invention, the improved laryngoscope includes in addition:
- a set of magnetic elements, so called magnetic bed, placed serially along the longitudinal axis of said blade, and having a respective magnetic vector that is perpendicular to surface of the above said blade;
- a lateral wall, placed close to the end of the extremity of above said blade;
- an external accessory, so called spiral tube, that comprises a metallic or magnetic element, placed along the radial surface, and that is free to translate tangentially in respect of said blade, so that said spiral tube is subject to an attractive force, created by interaction of said magnetic bed and said metallic or magnetic element, and the same attractive force keeps it in touch along the entire blade, all during the translation; and the extremity of said tube is directed, through said lateral wall, aligned to the longitudinal axis of said blade, so that it realizes a guide for pushing the same spiral tube towards the patient's mouth and inner air tract.

Furthermore, according to the invention, said blade of the improved laryngoscope is composed of an articulated structure, with at least three coplanar distal elements, said distal elements being free to rotate up, one in respect of the adjacent other, according to a respective pivot placed in respective joint points; and a manual command, i.e. a lever, is placed at the opposite part of the laryngoscope in respect of said handle, and is mechanically connected to said at least three coplanar distal elements, so that a forward action of lever causes a progressive lifting of each distal element, and a backward action of lever causes a progressive lowering of each distal element, until the starting coplanar position is reached again, and so that it is possible to adjust the geometrical shape of said blade of laryngoscope, in order to move the patient's anatomical tissues that are close to epiglottic vallecula, pulling the epiglottis down, and opening consequently a passage to trachea of the same patient.

BRIEF DESCRIPTION OF DRAWINGS

The present invention will now be described for illustrative but not limitative purposes, according to its preferred embodiments, with particular reference to figures of the enclosed drawings, wherein.

BEST MODES FOR CARRYING OUT THE INVENTION

It is here underlined that, in the following, only some of the many conceivable embodiments of the present invention will be described, and that they are just some particular examples that do not introduce any limitations, having the possibility to describe many other embodiments based on the disclosed technical solutions of the present invention.

Figure 1:
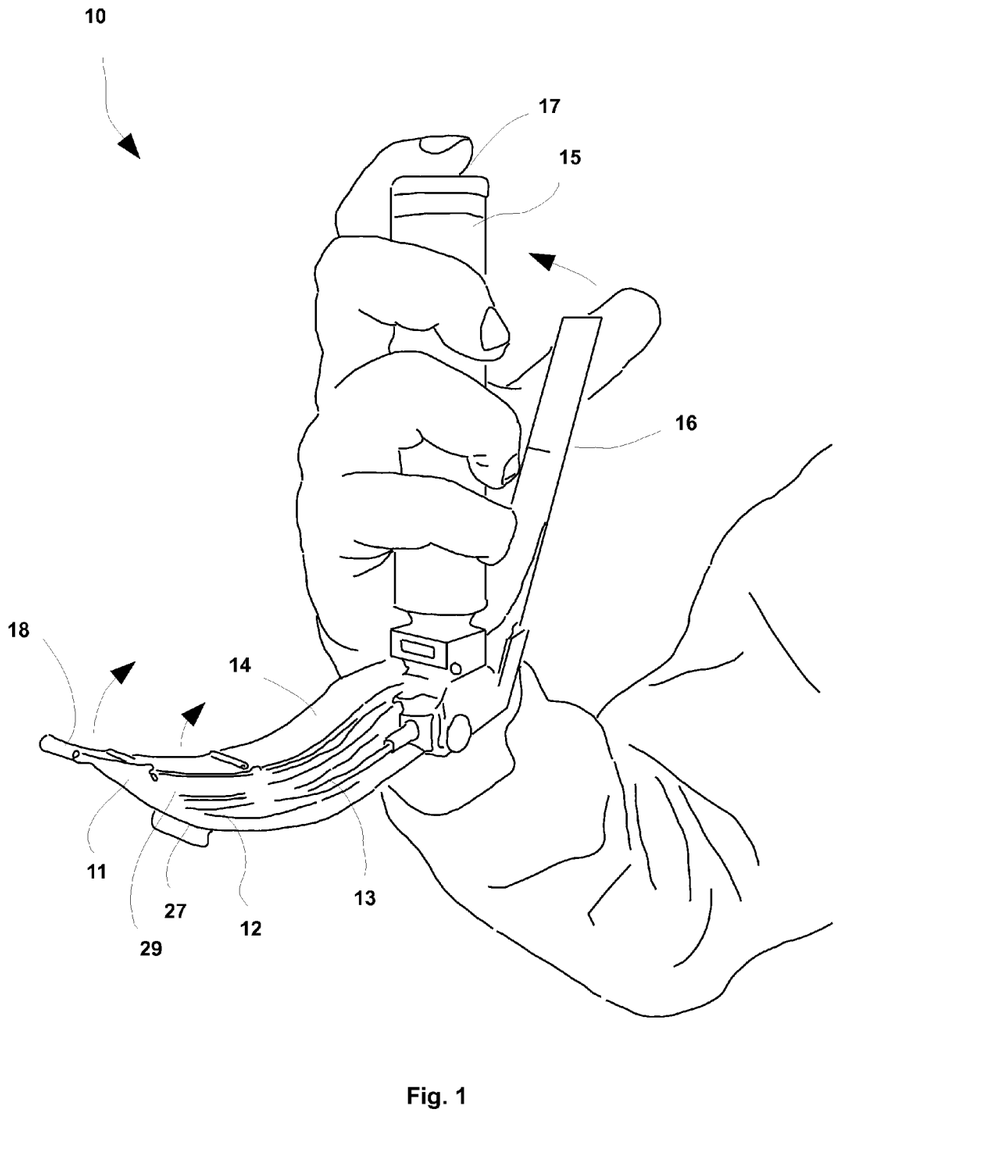
FIG. 1 is a perspective view of an improved laryngoscope, according to present invention, that is handled with reference to the actual operative protocols concerning endotracheal intubation of a patient.

In FIG. 1 it is illustrated an improved laryngoscope 10, that is handled with reference to the actual operative protocols concerning endotracheal intubation of a patient, that means with the handle 15 placed at the upper side, and the blade 14 in the front direction. In such a way, it is possible the insertion of the same blade 14 inside the mouth of a patient. According to specific principles of the invention, the ideal position of blade's extremity 14 is close to the so called epiglottic vallecula 24.

Figure 4:
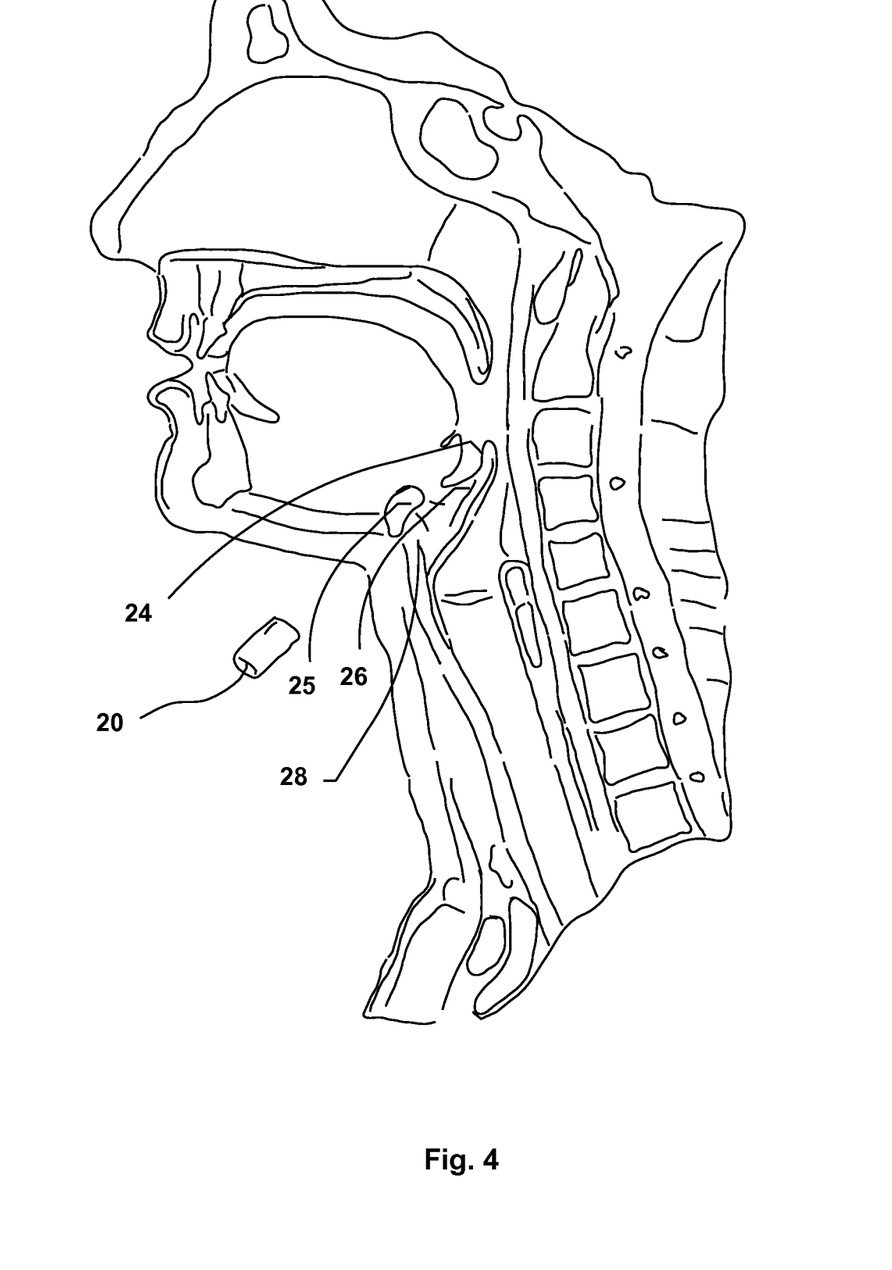
FIG. 4 is a lateral sectioned view of the anatomical parts of the human body, with particular reference to the part between the head and the neck, and related tissues, organs of mouth, larynx and air tracts are shown; in the same figure it is illustrated the ideal position of an inner magnet, immediately under the hyoid bone, oriented in direction of the thyrohyoid membrane.

In FIG. 4 the anatomical details of the human body are represented, with particular reference to the part between the head and the neck, and related tissues, organs of mouth, larynx and air tracts are shown.

The epiglottic vallecula 24 is located behind the tongue's root and before the epiglottis 26. Near the epiglottic vallecula 24 is located the hyoid bone 25, that is easily recognizable by a physician, just touching the patient at the upper front part of the throat.

Figure 3:
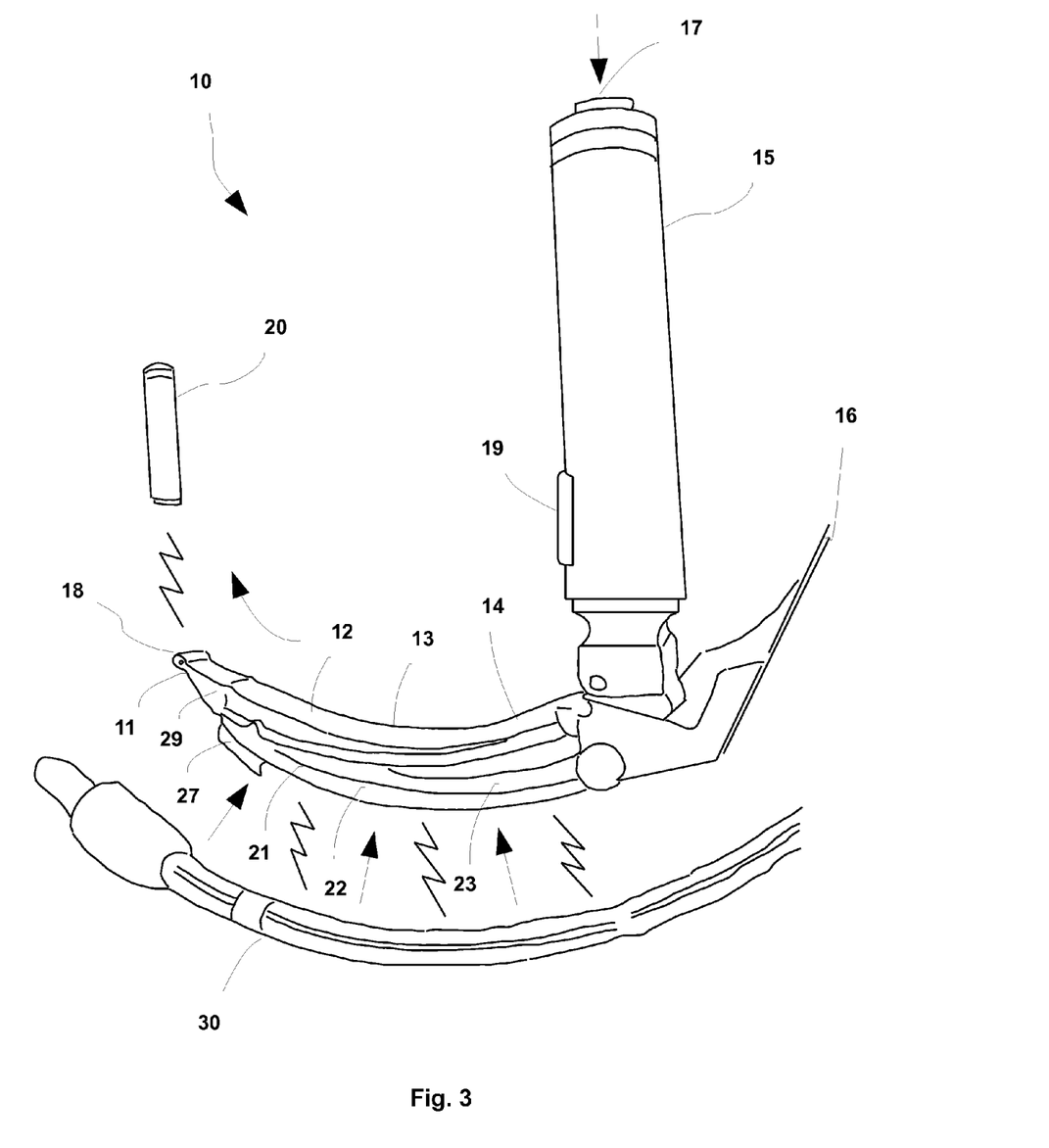
FIG. 3 is a lateral view of the same laryngoscope of FIG. 1, where the magnetic interactions are shown, between an outer magnet and a metallic spiral tube.

With reference to FIG. 3, blade 14 of laryngoscope 10 comprises a magnetic element 18 at its own remote extremity. Another magnetic element 20, having an opposite pole, in respect of the previous one, is placed by a physician at the outer front part of the patient, touching the throat, immediately under the hyoid bone 25, and oriented in direction of the thyrohyoid membrane 28. The two inner 18 and outer 20 magnets interact magnetically each other, expressing an attractive force. Using an hand in order to keep the outer magnet 20 in the above said position, and the other hand to handle the laryngoscope 10, with the blade 14 inside the patient's mouth, the physician can have a sensation of the attractive force, until the inner extremity of the instrument reaches the epiglottic vallecula 24. Naturally, the entire procedure should be visually guided by the same physician, enlighting the inner parts of the patient, using the small light bulb 29 that is embedded in the surface of the same blade 14. This light bulb 29 is powered by a set of batteries, that are usually located inside the handle 15 of the same laryngoscope 10.

Indeed, according to the present invention, the guide by magnetic interaction has been imagined especially for hard situations, like i.e. particular anatomical conformations of some patients, or a specific emergency (like i.e. hemorrhage of the rhino-pharyngeal tract) that does not allow a good visibility and that requires a procedure to be done in a very short time.

In order to have the possibility of variation for the intensity of magnetic force, that can be controlled by the same physician during the operations, the inner magnetic element 18 can be activated by a command button 17, placed at the top of handle 15. In this case, the magnetic element 18 can be composed of an electromagnet, i.e. a solenoid, able to create an induced magnetic field, that is directly proportional to the intensity of the coil's current. The same electromagnet is connected to a source of current, i.e. said set of batteries, and to a specific control circuit that can be calibrated using said command button 17.

Figure 6:
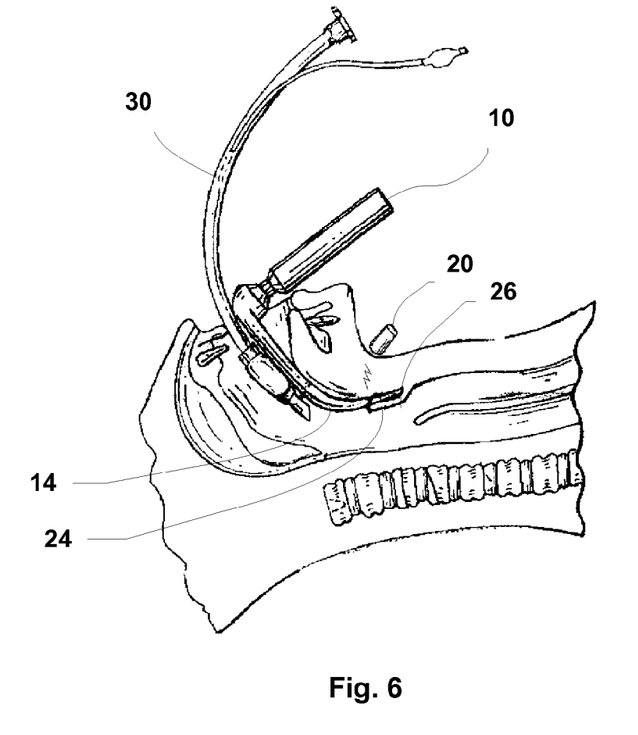
FIG. 6 is a lateral sectioned view of a patient, submitted to an endotracheal intubation, having a laryngoscope and a metallic spiral tube properly placed inside the mouth and larynx.

When the laryngoscope 10 is properly placed inside the mouth and upper air tracts of the patient, like i.e. that in FIG. 6, the physician can remove the outer magnet 20 and can start the standard intubation operations.

According to the present invention, laryngoscope 10 (illustrated in FIG. 2), can comprise additional mechanisms in order to adjust the geometrical shape of said blade 14 of laryngoscope 10, and in order to move the patient's anatomical tissues that are close to the epiglottic vallecula 24.

Figure 2:
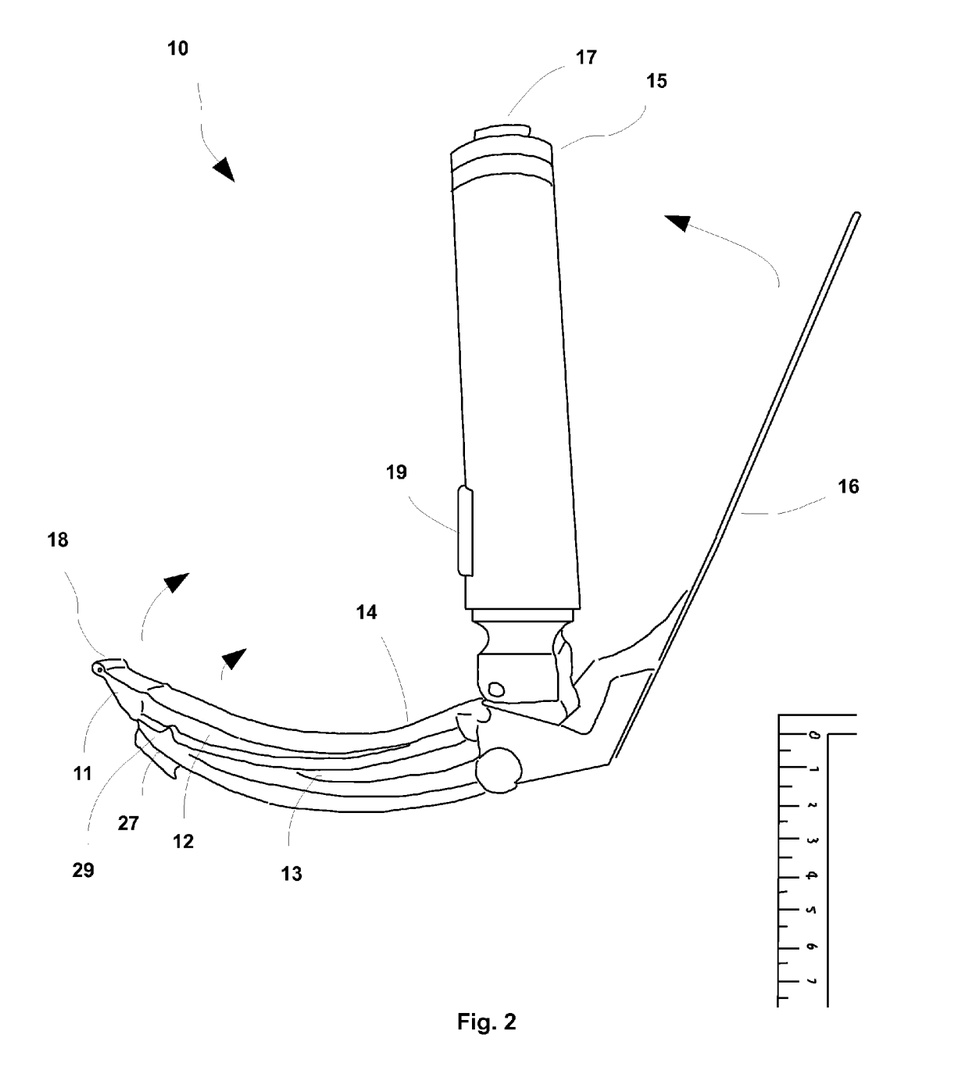
FIG. 2 is a lateral view of the same laryngoscope of FIG. 1, where the real dimensions are shown, according to a metric scale of reference.

The same blade 14 can be composed of an articulated structure with three coplanar distal elements 11, 12, 13. The distal elements 11, 12, are free to rotate up, one in respect of the adjacent other, according to a respective pivot placed in their inner joint points. An element with a manual command, i.e. a lever 16, is placed at the opposite part of laryngoscope 10 in respect of said handle 15. This lever 16 is mechanically connected to said distal elements 11, 12, so that a forward action of lever 16 causes a progressive lifting of each distal element 11, 12, and a backward action of lever 16 causes a progressive lowering of each distal element 11, 12, until the starting coplanar position is reached again.

Each distal element 11, 12, has a specific length and a specific angle in respect of the adjacent one, in order to be properly used in the real clinical cases.

The possibility to adjust the geometrical shape of said blade 14 makes it possible, for a physician, to move the patient's anatomical tissues that are close to the epiglottic vallecula 24, pulling the epiglottis 26 down, and opening consequently a passage to trachea of the same patient. This operation increases the visibility of larynx and other inner anatomical parts of the patient, especially in the above described difficult situations, where particular anatomical conformations of patient exist, or there are other emergency situations.

This solution is different in respect of the above said McCoy laryngoscope, for the reason that the blade's structure has a higher degree of freedom, and it gives the possibility to adapt the shape to many different real situations.

In an alternative embodiment of the present invention, said lifting and lowering actions of distal elements 11, 12, 13 can be done, instead through using a manual lever 16, through one or more electric engines, that are integrated in the same laryngoscope 10, and that are activated by a command button placed on handle 15.

This embodiment permits to obtain a very smooth and precise lifting of blade structures, decreasing the probability of trauma or shock for the inner tissues of the patient, during the intubation procedure.

Furthermore, according to the present invention, laryngoscope 10 (FIG. 3) comprises some additional mechanisms that permit a directional guide of an endotracheal tube 30 (FIG. 5) all during the time of insertion inside the patient's mouth and inner air tracts.

In particular, the laryngoscope 10 comprises a set of magnetic elements 21, 22, 23, so called magnetic bed, that are placed serially along the longitudinal axis of said blade 14. The same magnetic elements 21, 22, 23, have their magnetic vector that is perpendicular to surface of the above said blade 14.

Figure 5:
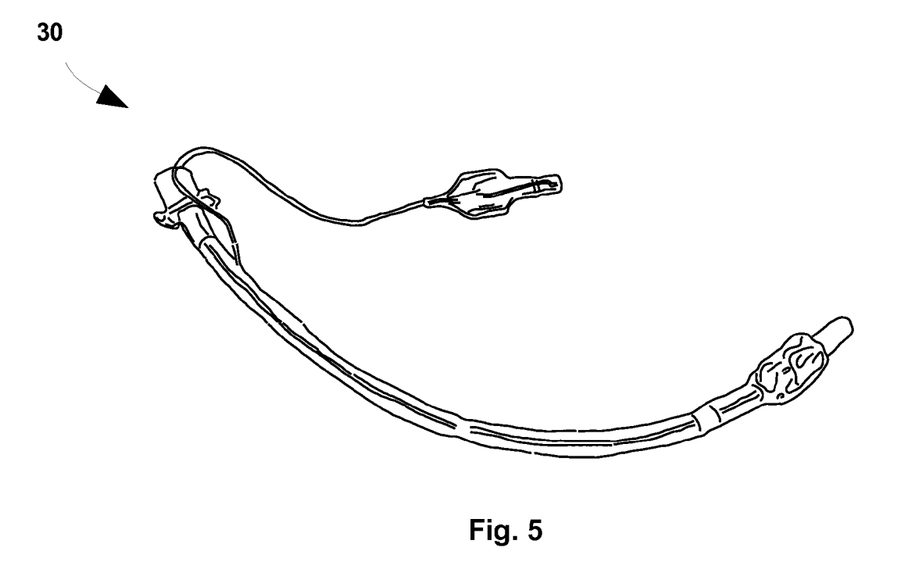
FIG. 5 is a lateral sectioned view of a metallic spiral tube, particularly suitable for an endotracheal intubation of a patient.

The endotracheal tube 30 is composed of a spiral tube 30, that comprises a metallic or magnetic element placed along the radial surface. The spiral tube 30 is well known in the prior art, because of its property of being not possible fold it up, that means a longitudinal section that can be constant in any situations. In the present invention, it is especially used for its metallic structure on surface, that makes it possible the interaction with said magnetic elements 21, 22, 23 of laryngoscope 10.

Figure 7:
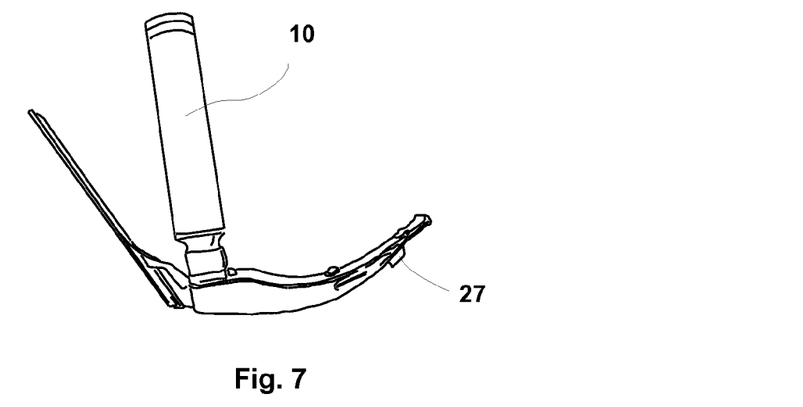
FIGS. 7, 8 and 9 are respective lateral views of a metallic spiral tube, like that in FIG. 5, in different positions according to different steps of endotracheal intubation of a patient.
Figure 8:
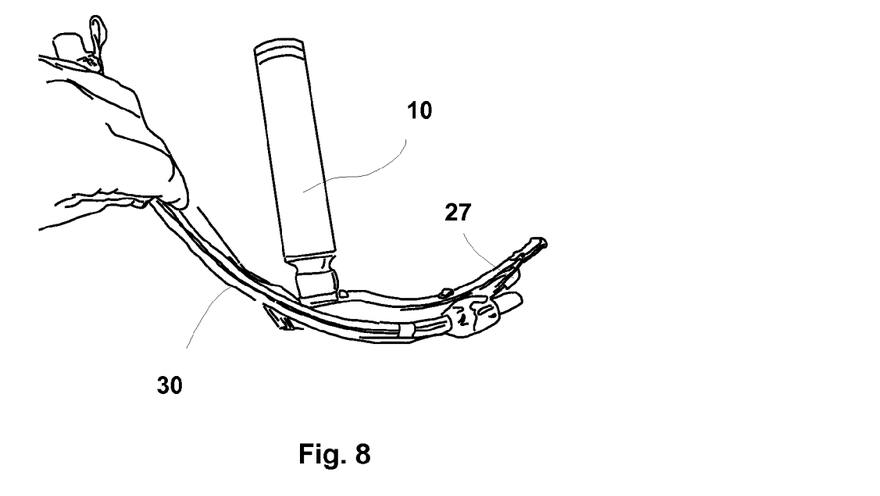
Figure 9:
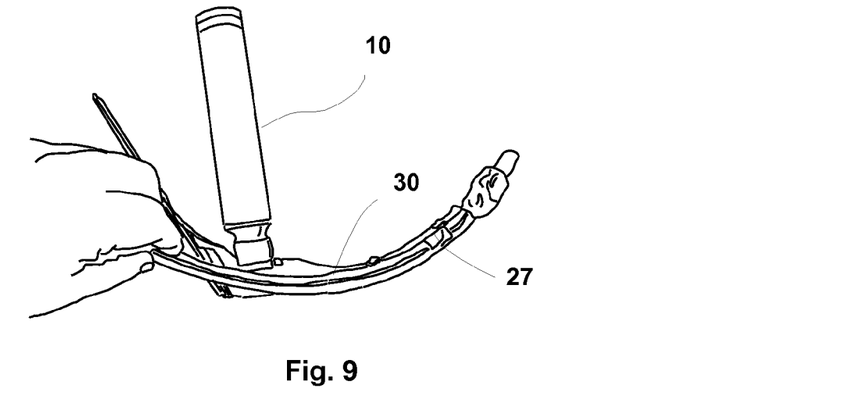

In fact, the magnetic bed generates an attractive force that keeps the spiral tube 30 in touch along the blade 14, all during the time of insertion inside the patient's mouth and inner air tracts. In FIGS. 7, 8 and 9, it is illustrated a sequence of insertion of a spiral tube 30 like that shown in FIG. 5.

A lateral wall 27 can be placed at the extremity of blade 14, so that said tube 30 can be aligned to the same blade 14, and the operation of pushing it inside the trachea or pulling it outside is easier. This lateral wall 27 can be placed at different distances on blade 14 or it can be placed along the entire length of blade 14.

In an alternative embodiment of the present invention, the attractive magnetic force, that keeps the spiral tube 30 continuously in touch with said blade 14, can be activated by a proper switch, using a command button 19 placed at the lateral part of handle 15.

In this case, the above set of magnetic elements 21, 22, 23, would be composed of a set of respective electromagnets, i.e. a set of solenoids, each of them able to create an induced magnetic field, that is directly proportional to the intensity of the current of coil. This current depends on position of switch 19, so that the "on" position corresponds to a specific level of current, "off" position corresponds to a ground level (zero). In this way, the position of switch 19 defines the existence or not of an induced magnetic field, and then the existence or not of an attractive force on spiral tube 30. This solution results particularly useful when the physician, after installation of an endotracheal tube 30, should remove the same laryngoscope 10, without the risk of pulling out also the tube 30 that is magnetically connected to it, and in all the other cases where it is necessary to extract the tube 30 without keeping the magnetic guide activated, in order to guarantee low stress for anatomical structures of the patient. In fact, these structures could be compressed in the space between tube 30 that translates, and the fixed distal extremity 11 of blade 14 (i.e. in a situation where the tube should be recalled of few centimeters, because it is in the wrong position or it has been directed badly during the first attempts of endotracheal intubation).

In an alternative embodiment of the present invention, the endotracheal tube is exactly the same like the others from the prior art, where a "rosary"-shaped stylet is inserted inside. This is a stylet having a structure composed of a certain number of single elements (nodes), that are connected each other in order to define a chain. Each of these nodes is indeed a metallic or a magnetic element, so that it can interact magnetically with the above said elements 21, 22, 23 of laryngoscope 10. In this way, the "rosary"-shaped stylet, properly inserted inside the endotracheal tube, realizes a guide sensing the attractive force of blade 14, and keeping the endotracheal tube in touch along the insertion in the patient's mouth.

However, all these described embodiments of the present invention do not exclude a standard use of the improved laryngoscope 10.

In example, a standard stylet can be used in order to give a proper shape to the endotracheal tube, and the intubation can be done according to the well known techniques. Furthermore, the same endotracheal tube, whether it has been installed according to the previously known techniques, whether it has been guided by magnetic elements as above described, can be a specific support for a fiberscopy. In that case, the endotracheal tube would represent a structure, where a microcamera can be inserted inside. This microcamera, properly connected to an optical fiber, permits to see, and eventually to visualize on a screen, the inner anatomical structures of the same patient, and can represent a really useful instrument in order to help medical staff to recognize anomalies, and to provide a diagnosis concerning the existence of specific pathologies.

Therefore, the above examples show that the present invention achieves all the proposed objectives. In particular, it proposes an improved laryngoscope that allows an endotracheal intubation of a patient, where the position of its own blade's extremity is guided by an outer magnetic element, towards the so called epiglottic vallecula.

Then, once placed, the same device permits to move the patient's anatomical tissues that are close to the epiglottic vallecula, pulling the epiglottis down, and to open consequently a passage to trachea of the same patient. This procedure gives a better view of larynx and other inner anatomical parts of the same patient.

Again, according to the invention, the same laryngoscope guarantees a directional guide all during the time of insertion of an endotracheal tube inside the patient's mouth and air tracts.

Furthermore, according to the invention, the use of laryngoscope results to be particularly fast, precise and comfortable, and allows an intubation procedure that can be done by a unique physician.

The present invention has been described for illustrative but not limitative purposes, according to its preferred embodiments, but it is clear that modifications and/or changes can be introduced by those skilled in the art without departing from the relevant scope, as defined in the enclosed claims.

The invention claimed is:

1. An improved laryngoscope, especially suitable to be used in a procedure of endotracheal intubation of a patient, comprising:
   a handle having a set of batteries are installed therein; and
   a blade, jointed to said handle with an "L" shape, said blade including a small light bulb having terminals that are electrically connected to respective poles of said set of batteries; said blade configured for being pushed inside the patient's mouth, and said light bulb being able to illuminate the inner parts of the same patient;

said blade further comprising an inner magnetic element that is situated distally at an extremity thereof, said inner magnetic element being able to interact with an outer magnetic element, having an opposite pole, said outer magnetic element being configured to touch the outside of the patient's throat, immediately under the hyoid bone and oriented in direction of the thyrohyoid membrane, such that when said outer magnetic element is so placed, said extremity of said blade is subject to a first attractive force, created by interaction of said inner and outer magnetic elements, and is consequently placed close to the patient's epiglottic vallecula;

a set of magnetic elements forming a magnetic bed, said magnetic elements being positioned serially along a longitudinal axis of said blade, and having a respective magnetic vector that is perpendicular to a radial surface of said blade; a lateral wall, positioned close to an end of the extremity of said blade and aligned along the longitudinal axis of the same; a spiral tube, said spiral tube being an external accessory comprising a metallic or magnetic element, and being configured such that when it is positioned along the radial surface of said blade, said tube is subject to a second attractive force, created by an interaction between said magnetic bed and said metallic or magnetic element, whereby said tube is free to translate longitudinally along said radial surface of said blade while still being kept in touch with said blade by said second attractive force and an extremity of said spiral tube is directed along the longitudinal axis of said blade by said lateral wall whereby said spiral tube is directed towards the patient's mouth and inner air tract;

said blade further comprising an articulated structure with at least three coplanar distal elements, at least two of said distal elements being free to rotate with respect to an adjacent other about a respective pivot; and a manual command the positioned opposite, relative to the handle, of the at least three coplanar distal elements, said manual command being mechanically connected to said at least two distal elements, so that a forward action of the manual command causes a progressive rotation toward the handle of each of said at least two distal elements, and a backward action of the manual command causes a progressive rotation away from the handle of each of said at least two distal elements until the starting coplanar position is reached again; whereby the use of the articulated structure in conjunction with the manual command makes it possible to adjust the geometrical shape of said blade of the laryngoscope, in order to move the patient's anatomical tissues that are close to the epiglottic vallecula, pull the epiglottis down, and open a passage to the patient's trachea.

2. An improved laryngoscope, especially suitable to be used in a procedure of endotracheal intubation of a patient, according to claim 1, wherein:

said inner magnetic element comprises an electromagnet incorporating a coil, wherein the electromagnet is able to create an induced magnetic field, a strength of which, and of the first attractive force, is directly proportional to an intensity of current in the coil;

said electromagnet being connected to a source of current and to a first control circuit that is tuned using a potentiometer, said potentiometer including a command button placed at the top of said handle, said first control circuit being adapted for calibrating the intensity of current such that said intensity is directly proportional to a level of pressure on said command button, whereby adjusting the level of pressure on said command button causes an adjustment in the intensity of current and consequently the strength of the induced magnetic field and of the first attractive force.

3. An improved laryngoscope, especially suitable to be used in a procedure of endotracheal intubation of a patient, according to claim 1, wherein:

said set of magnetic elements comprises a set of respective electromagnets incorporating a set of respective coils, wherein the set of respective electromagnets is able to create a second induced magnetic field, a strength of which, and of the second attractive force, is directly proportional to a second intensity of current in the set of respective coils;

said set of electromagnets being connected to a second source of current and to a second control circuit that is connected to a switch including a second command button and having an "on" position and an "off" position, said switch being placed at a lateral part of said handle, said second control circuit being adapted for calibrating the second intensity of current in conjunction with said switch such that placing the switch in the "on" position causes the second intensity of current in the set of respective coils to be equal to a specific level and the strength of the second induced magnetic field and of the second attractive force to be directly proportional to said specific level, and placing the switch in the "off" position causes the second intensity of current in the set of respective coils to be equal to ground level (zero) and the strength of the second induced magnetic field and of the second attractive force to be zeroed.

4. An improved laryngoscope, especially suitable to be used in a procedure of endotracheal intubation of a patient, according to claim 1, further comprising:

said lateral wall extending along an entire length of the blade whereby actions of pushing the tube inside the trachea and pulling the tube out of the trachea are both made easier than would be the case if said lateral wall did not so extend.

5. An improved laryngoscope, especially suitable to be used in a procedure of endotracheal intubation of a patient, according to claim 1, wherein:

said manual command comprises a lever.

6. An improved laryngoscope, especially suitable to be used in a procedure of endotracheal intubation of a patient, according to claim 2, wherein:

said source of current comprises said set of batteries.

7. An improved laryngoscope, especially suitable to be used in a procedure of endotracheal intubation of a patient, according to claim 3, wherein:

said second source of current comprises said set of batteries.

8. An improved laryngoscope, especially suitable to be used in a procedure of endotracheal intubation of a patient, comprising:

a handle having a set of batteries are installed therein; and
a blade, jointed to said handle with an "L" shape, said blade including a small light bulb having terminals that are electrically connected to respective poles of said set of batteries; said blade configured for being pushed inside the patient's mouth, and said light bulb being able to illuminate the inner parts of the same patient;

said blade further comprising an inner magnetic element that is situated distally at an extremity thereof, said inner magnetic element being able to interact with an outer magnetic element, having an opposite pole, said outer magnetic element being configured to touch the outside of the patient's throat, immediately under the hyoid bone and oriented in direction of the thyrohyoid membrane, such that when said outer magnetic element is so placed, said extremity of said blade is subject to a first attractive force, created by interaction of said inner and outer magnetic elements, and is consequently placed close to the patient's epiglottic vallecula;

a set of magnetic elements forming a magnetic bed, said magnetic elements being positioned serially along a longitudinal axis of said blade, and having a respective magnetic vector that is perpendicular to a radial surface of said blade; a lateral wall, positioned close to an end of the extremity of said blade and aligned along the longitudinal axis of the same; a spiral tube, said spiral tube being an external accessory comprising a metallic or magnetic element, and being configured such that when it is positioned along the radial surface of said blade, said tube is subject to a second attractive element, whereby said tube is free to translate longitudinally along said radial surface of said blade while still being kept in touch with said blade by said second attractive force and an extremity of said spiral tube is directed along the longitudinal axis of said blade by said lateral wall whereby said spiral tube is directed towards the patient's mouth and inner air tract;

said blade further comprising an articulated structure with at least three coplanar distal elements, at least two of said distal elements being free to rotate with respect to an adjacent other about a respective pivot; one or more electric engines integrated in said laryngoscope and connected to said at least two distal elements; a third command button placed on said handle and electrically connected to said one or more electric engines, whereby a first activation of said third command button causes a progressive rotation toward the handle of each of said at least two distal elements, and a second activation of said third command button causes a progressive rotation away from the handle of each of said at least two distal elements until the starting coplanar position is reached again; whereby the use of the articulated structure in conjunction with the one or more electric engines and third command button makes it possible to adjust the at least two distal elements smoothly and precisely, decreasing the probability of trauma or shock for the inner tissues of the patient.

9. An improved laryngoscope, especially suitable to be used in a procedure of endotracheal intubation of a patient, comprising:

a handle having a set of batteries are installed therein; and a blade, jointed to said handle with an "L" shape, said blade including a small light bulb having terminals that are electrically connected to respective poles of said set of batteries; said blade configured for being pushed inside the patient's mouth, and said light bulb being able to illuminate the inner parts of the same patient;

said blade further comprising an inner magnetic element that is situated distally at an extremity thereof, said inner magnetic element being able to interact with an outer magnetic element, having an opposite pole, said outer magnetic element being configured to touch the outside of the patient's throat, immediately under the hyoid bone and oriented in direction of the thyrohyoid membrane, such that when said outer magnetic element is so placed, said extremity of said blade is subject to a first attractive force, created by interaction of said inner and outer magnetic elements, and is consequently placed close to the patient's epiglottic vallecula;

a set of magnetic elements forming a magnetic bed, said magnetic elements being positioned serially along a longitudinal axis of said blade, and having a respective magnetic vector that is perpendicular to a radial surface of said blade; a lateral wall, positioned close to an end of the extremity of said blade and aligned along the longitudinal axis of the same; an endotracheal tube, said endotracheal tube being an external accessory having a "rosary"-shaped stylet inserted therein, said stylet having two or more metallic or magnetic nodes, with each of said metallic or magnetic nodes being chained to an adjacent other; said tube being configured such that when it is positioned along the radial surface of said blade, said stylet is subject to a third attractive force, created by an interaction between said magnetic bed and said metallic or magnetic nodes, whereby said stylet is free to translate longitudinally within said tube while still being kept in close proximity with said blade by said third attractive force and an extremity of said spiral tube is directed along the longitudinal axis of said blade by said lateral wall whereby said spiral tube is directed towards the patient's mouth and inner air tract;

said blade further comprising an articulated structure with at least three coplanar distal elements, at least two of said distal elements being free to rotate with respect to an adjacent other about a respective pivot; and a manual command positioned opposite, relative to the handle, of the at least three coplanar distal elements, said manual command being mechanically connected to said at least two distal elements, so that a forward action of the manual command causes a progressive rotation toward the handle of each of said at least two distal elements, and a backward action of the manual command causes a progressive rotation away from the handle of each of said at least two distal elements until the starting coplanar position is reached again; whereby the use of the articulated structure in conjunction with the manual command makes it possible to adjust the geometrical shape of said blade of the laryngoscope, in order to move the patient's anatomical tissues that are close to the epiglottic vallecula, pull the epiglottis down, and open a passage to the patient's trachea.

* * * * *